United States Patent
Yamada et al.

(10) Patent No.: US 10,011,853 B2
(45) Date of Patent: Jul. 3, 2018

(54) YEAST HAVING XYLOSE ASSIMILATION ABILITY AND ETHANOL PRODUCTION ABILITY

(71) Applicant: YAMAGUCHI UNIVERSITY, Yamaguchi (JP)

(72) Inventors: Mamoru Yamada, Yamaguchi (JP); Sukanya Nitiyon, Yamaguchi (JP); Chansom Keo-Oudone, Vientiane (LA)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 0 days.

(21) Appl. No.: 15/305,105

(22) PCT Filed: Apr. 22, 2015

(86) PCT No.: PCT/JP2015/002175
§ 371 (c)(1),
(2) Date: Oct. 19, 2016

(87) PCT Pub. No.: WO2015/166645
PCT Pub. Date: Nov. 5, 2015

(65) Prior Publication Data
US 2017/0051319 A1     Feb. 23, 2017

(30) Foreign Application Priority Data
Apr. 28, 2014    (JP) ................................. 2014-092206

(51) Int. Cl.
*C12P 7/06*     (2006.01)
*C12N 1/16*     (2006.01)
*C12R 1/645*     (2006.01)

(52) U.S. Cl.
CPC .................. *C12P 7/06* (2013.01); *C12N 1/16* (2013.01); *C12R 1/645* (2013.01); *Y02E 50/17* (2013.01)

(58) Field of Classification Search
CPC ........................................................ C12P 7/06
USPC ................................................ 435/252.3, 161
See application file for complete search history.

(56) References Cited

FOREIGN PATENT DOCUMENTS

| | | |
|---|---|---|
| JP | 2005058055 A | 3/2005 |
| JP | 2012183013 A | 9/2012 |
| JP | 2012210169 A | 11/2012 |
| JP | 2012231794 A | 11/2012 |
| JP | 2013021947 A | 2/2013 |
| JP | 2013042727 A | 3/2013 |

OTHER PUBLICATIONS

Carlson, Marian "Glucose repression in yeast" Current Opinion in Microbiology 2:202-207 (1999).
Rodrussamee, Nadchanok et al. "Growth and ethanol fermentation ability on hexose and pentose sugars and glucose effect under various conditions in thermotolerant yeast *Kluyveromyces marxianus*", Appl. Microbiol. Biotechnol., 2011, vol. 90, pp. 1573-1586.
Nonklang, Sanom et al. "High-Temperature Ethanol Fermentation and Transformation with Linear DNA in the Thermotolerant Yeast *Kluyveromyces marxianus* DMKU3-1042", Appl.Environ. Microbiol., 2008, vol. 74, pp. 7514-7521, p. 7516, right column, line 6 to p. 7517, left column, line 2, fig. 1A.
International Report on Patentability [PCT/JP2015/002175] dated Nov. 10, 2016.

*Primary Examiner* — Tekchand Saidha
(74) *Attorney, Agent, or Firm* — Edwin S. Flores; Daniel J. Chalker; Chalker Flores, LLP

(57) ABSTRACT

An object is to provide a thermotolerant yeast capable of assimilating xylose to produce ethanol or a mutant strain thereof and a method for producing ethanol by assimilation of xylose. There is used a yeast, *Kluyveromyces marxianus* strain No. 21 (accession number: NITE BP-01739), or a mutant strain thereof that has xylose assimilation ability and ethanol production ability when cultured at 30° C. under aerobic conditions using a culture medium containing xylose as a sugar source. Also performed is a method for producing ethanol, comprising culturing the yeast or the mutant strain thereof under aerobic conditions using a culture medium containing xylose as a sugar source.

3 Claims, 3 Drawing Sheets

[Figure 1]
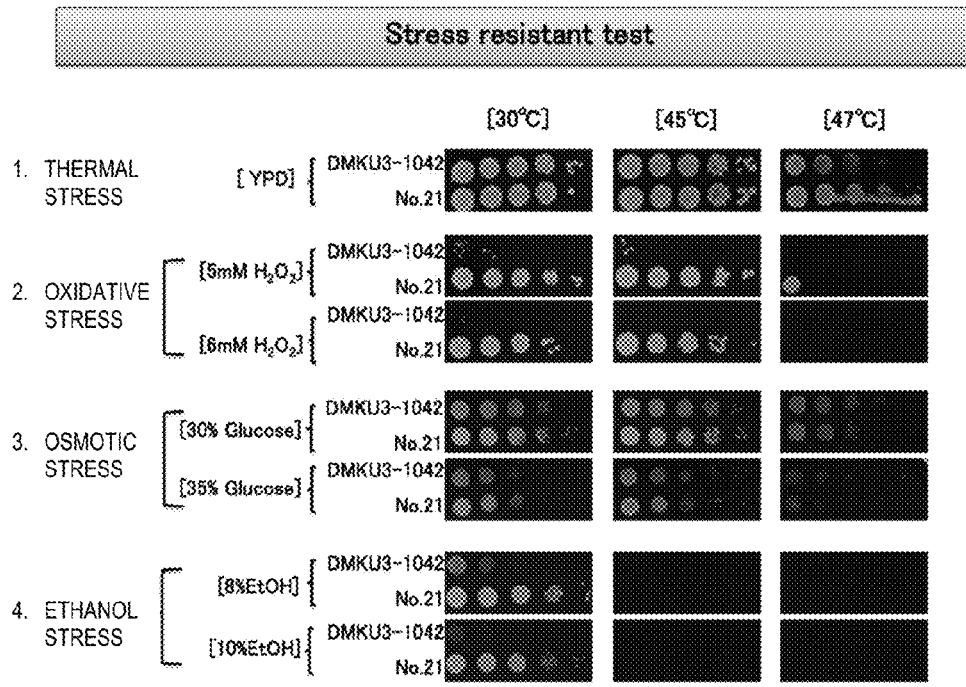
[Figure 2]
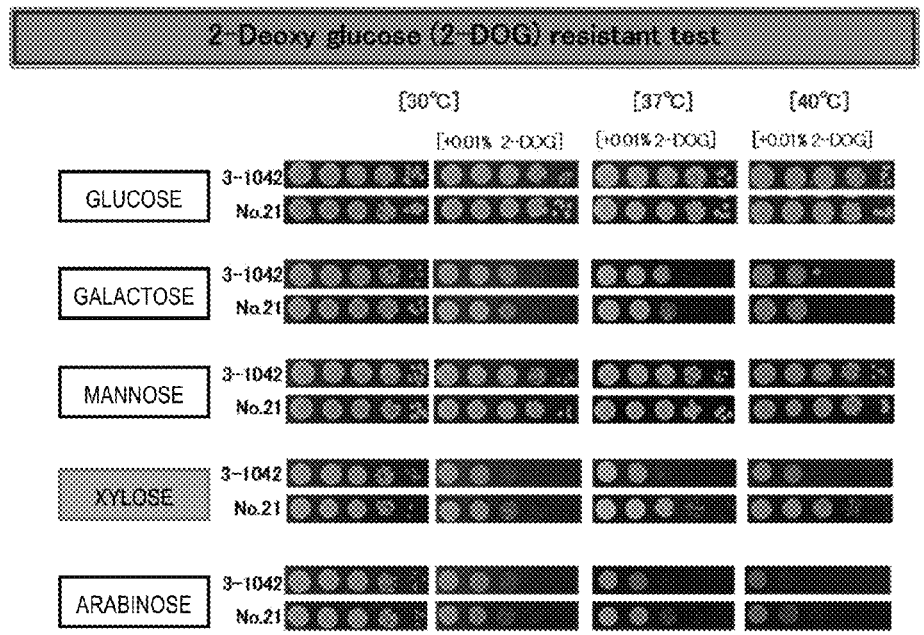

[Figure 3]
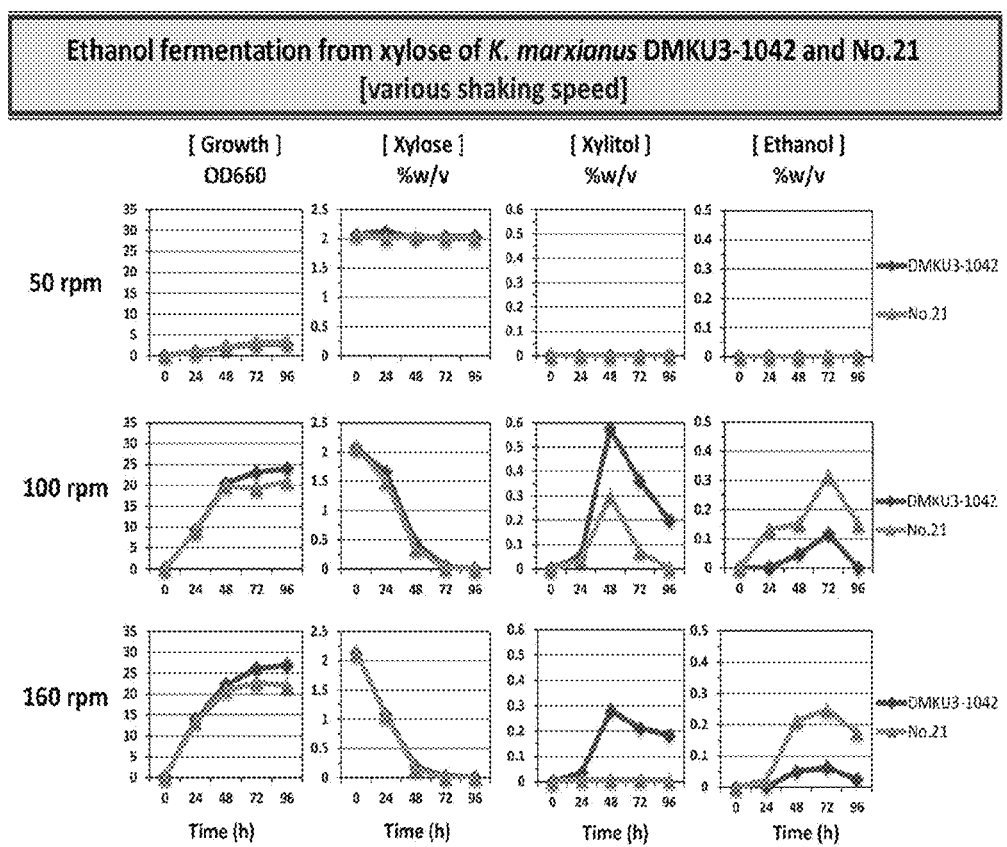

[Figure 4]
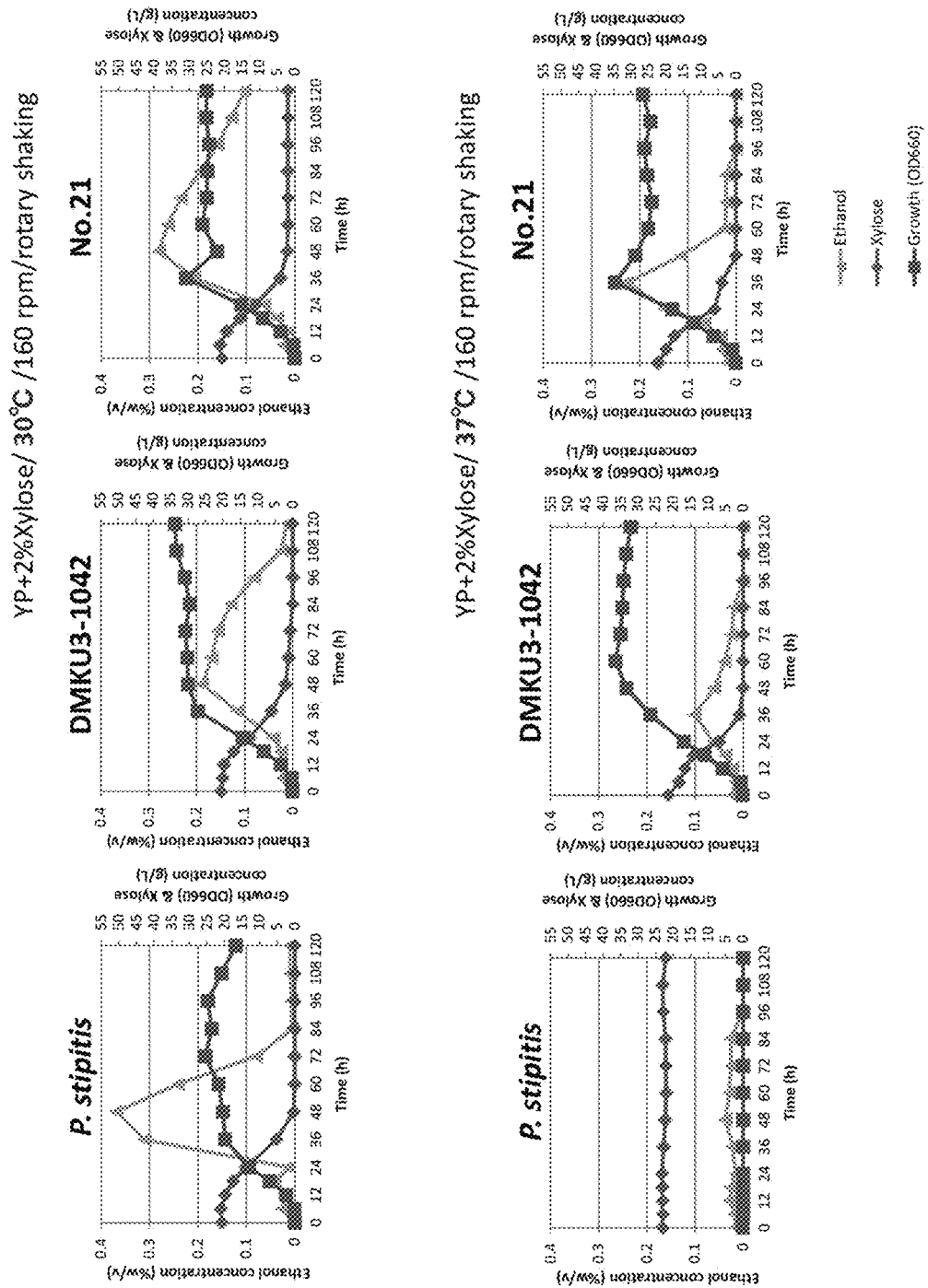

YEAST HAVING XYLOSE ASSIMILATION ABILITY AND ETHANOL PRODUCTION ABILITY

CROSS-REFERENCE TO RELATED APPLICATIONS

This application is the National Stage of International Application No. PCT/JP2015/002175, filed on Apr. 22, 2015 claiming the priority of JP 2014-092206 filed on Apr. 28, 2014, the content of each of which is incorporated by reference herein.

TECHNICAL FIELD

The present invention relates to a yeast having xylose assimilation ability and ethanol production ability and to a method for producing ethanol, and more particularly relates to a yeast, *Kluyveromyces marxianus* strain No. 21 (accession number: NITE BP-01739), or a mutant strain thereof that has xylose assimilation ability and ethanol production ability when cultured at 30° C. under aerobic conditions using a culture medium containing xylose as a sugar source and to a method for producing ethanol using the yeast or the mutant strain thereof.

BACKGROUND ART

Bioethanol, which is produced from various raw materials through fermentation by microorganisms, has been receiving attention as global warming has become a worldwide problem. Bioethanol is ethanol produced by fermentation of a sugar formed from biomass, and is considered promising for use as an alternative fuel to fossil fuels, in particular gasoline, since it is a renewable natural source of energy and does not increase the amount of atmospheric carbon dioxide when burned.

DEPOSIT OF BIOLOGICAL MATERIAL

The following biological material has been deposited under the terms of the Budapest Treaty with the National Laboratory for Genetic Resources Preservation, 1111 S. Mason Street, Fort Collins, Colo., USA, and given the following number:

| Deposit | Accession Number | Date of Deposit |
|---|---|---|
| *Kluyveromyces marxianus* strain No. 21 | BP-01739 | Mar. 16, 2015 |

Deposit Accession Number Date of Deposit
*Kluyveromyces marxianus* strain No. 21 BP-01739 Mar. 16, 2015

The seeds have been deposited under conditions that assure that access to the seeds will be available during the pendency of this patent application to one determined by the Commissioner of Patents and Trademarks to be entitled thereto under 37 C.F.R. § 1.14 and 35 U.S.C. § 122. The deposit represents a yeast capable of xylose assimilation and ethanol production. The deposit is available as required by foreign patent laws in countries wherein counterparts of the subject application, or its progeny are filed. However, it should be understood that the availability of a deposit does not constitute a license to practice the subject invention in derogation of patent rights granted by government action.

At present, industrial production of bioethanol employs, as raw materials, sugars derived from sugar cane, molasses, and the like or starches derived from corn, potato, cassava, and the like. This has caused the problem of competition with production of food and feed. Under such circumstances, lignocellulosic biomass derived from herbaceous plant, wood scrap, and the like, has been receiving attention as a next-generation raw material of bioethanol. Lignocellulosic biomass is composed of cellulose, hemicellulose, lignin, and the like. Studies on ethanol production using lignocellulosic biomass as a raw material have been conducted thus far, and examples of proposed methods for saccharifying lignocellulose by physical and chemical treatment to produce ethanol include: a treatment method using a weed and consisting of an energization step of immersing the weed in a buffer solution and applying a voltage to the buffer solution to obtain an energized product of the weed, a saccharification step of converting the energized product into a saccharified product with an enzyme, and a fermentation step of adding a yeast to the saccharified product as a raw material to allow ethanol fermentation to take place (see patent document 1); and a pretreatment method used in a method for producing a sugar by an enzymatic saccharification treatment and then producing ethanol from the sugar by ethanol fermentation, the pretreatment method being characterized by digesting lignocellulosic biomass using an aqueous ethanol solution of a metal hydroxide such as sodium hydroxide before the enzymatic saccharification treatment for producing a sugar (see patent document 2). However, the physical and chemical treatment of lignocellulose poses unresolved problems in terms of cost and environmental load, and has yet to be put into practice.

Xylose is a type of pentose and accounts for about 25% of lignocellulose. Successful use of such xylose as a raw material for bioethanol production is expected to extend the application of lignocellulosic biomass. However, *saccharomyces cerevisiae*, which is a typical yeast for ethanol production, lacks xylose assimilation ability and, therefore, xylose cannot serve as a raw material for ethanol production when *saccharomyces cerevisiae* is used.

In recent years, microorganisms having xylose assimilation ability imparted by gene recombination or the like have been proposed, and examples thereof include: a fungal host cell transformed with a nucleic-acid construct containing a nucleotide sequence that encodes xylose isomerase, the host cell being endowed with the ability to use xylose as a carbon source (see patent document 3); a mutant yeast belonging to genus *Kluyveromyces*, the mutant yeast being modified by reducing the expression of ADH1 gene and ADH4 gene so that the mutant yeast provides an increase in the ethanol yield from xylose (see patent document 4); and microorganisms in which the expression ability of a glycine-synthesizing protein gene and/or a methionine-synthesizing protein gene has been lost and into which a xylose metabolic enzyme gene has been introduced, the microorganisms thus having an increased xylose assimilation rate (see patent document 5).

However, since such gene-altered microorganisms are microorganisms that do not exist in nature, ethanol production using the gene-altered microorganisms is subject to many restrictions as to so-called physical confinement in view of ecosystem effect; for example, a highly hermetic installation must be provided to prevent leakage of the gene-altered microorganisms from a fermentation tank in which ethanol production is carried out. Furthermore, an auxiliary system for addressing such leakage is also needed, and full sterilization must be done for disposal after completion of fermentation, which leads to high cost. Additionally, as for yeasts, there is a well-known phenomenon, called "glucose repression", in which the presence of glucose obstructs the pathways involved in metabolism of other sugars (see Non-patent document 1), and this phenomenon has been a challenge to ethanol production from biomass composed of various sugars including glucose.

The present inventors have studied ethanol production using *Kluyveromyces marxianus* strain DMKU3-1042, which is a thermotolerant, ethanol-producing yeast, and using various pentoses and hexoses as sugar sources (see Non-patent document 2). Having thermotolerance, the *Kluyveromyces marxianus* strain DMKU3-1042 allows fermentation at high temperatures. The use of the *Kluyveromyces marxianus* strain DMKU3-1042 can thus reduce the cost required for an installation for cooling a culture fluid made hot by fermentation heat generated in a fermentation step; however, there has been a problem in that the ethanol productivity is very low when only a pentose is used as a sugar source.

PRIOR ART DOCUMENTS

Patent Documents

Patent document 1: Japanese unexamined Patent Application Publication No. 2005-058055
Patent document 2: Japanese unexamined Patent Application Publication No. 2013-042727
Patent document 3: Japanese unexamined Patent Application Publication No. 2012-231794
Patent document 4: Japanese unexamined Patent Application Publication No. 2012-210169
Patent document 5: Japanese unexamined Patent Application Publication No. 2012-183013

Non-Patent Documents

Non-patent document 1: Marian C (1999) Current Opinion in Microbiology 2:202-207
Non-patent document 2: Rodrussamee N et al. (2011) Appl. Microbiol. Biotechnol. 90:1573-1586

SUMMARY OF THE INVENTION

Object to be Solved by the Invention

As described above, methods using microorganisms to assimilate xylose and produce ethanol have been proposed; however, the current situation is that a strain capable of assimilating xylose to produce ethanol cost-effectively and efficiently has not yet been obtained. It is therefore an object of the present invention to provide a thermotolerant yeast capable of assimilating xylose to produce ethanol or a mutant strain thereof and a method for producing ethanol by assimilation of xylose.

Means to Solve the Object

To solve the above object, the present inventors have first obtained a thermotolerant yeast growable even at 47° C. in Laos. As a result of further investigation of the characteristics of the thermotolerant yeast, the present inventors have found that the yeast can assimilate xylose when cultured at 40° C. in the presence of glucose and that the yeast can assimilate xylose to produce ethanol when cultured under aerobic conditions using xylose as the sole sugar source, thereby completing the present invention.

That is, the present invention relates to: [1] a yeast, *Kluyveromyces marxianus* strain No. 21 (accession number: NITE BP-01739), or mutant strain thereof that has xylose assimilation ability and ethanol production ability when cultured at 30° C. under aerobic conditions using a culture medium containing xylose as a sugar source; and [2] a method for producing ethanol, comprising culturing the yeast or mutant strain thereof according to [1] under aerobic conditions using a culture medium containing xylose as a sugar source.

Effect of the Invention

According to the present invention, it is possible to provide a thermotolerant yeast capable of assimilating xylose to produce ethanol. Additionally, the yeast or the mutant strain thereof according to the present invention is capable of assimilating xylose even at 40° C., which is why the use of the yeast or the mutant strain thereof according to the present invention for producing ethanol can reduce the cost required for an installation for cooling a culture fluid. Furthermore, the yeast or the mutant strain thereof according to the present invention has glucose resistance, and thus allows efficient ethanol production even when a saccharified solution derived from lignocellulosic biomass is used as a sugar source.

BRIEF DESCRIPTION OF DRAWINGS

FIG. 1 is a diagram showing the results of various stress resistant tests conducted on *Kluyveromyces marxianus* strain No. 21.
FIG. 2 is a diagram showing the results of glucose resistant tests conducted on *Kluyveromyces marxianus* strain No. 21.
FIG. 3 is a diagram showing the results of tests of ethanol production from xylose which were conducted on *Kluyveromyces marxianus* strain No. 21.
FIG. 4 is a diagram showing the results of tests of ethanol production from xylose which were conducted on *Kluyveromyces marxianus* strain No. 21 under culture conditions at 30° C. or at 37° C.

MODE OF CARRYING OUT THE INVENTION

The yeast according to the present invention, *Kluyveromyces marxianus* strain No. 21 (sometimes simply referred to as "strain No. 21" hereinafter), is a naturally-derived strain isolated by the present inventors in Laos. The strain was deposited to Patent Microorganisms Depositary of National Institute of Technology and Evaluation (NITE), located at Room 122, 2-5-8, Kazusakamatari, Kisarazu-shi, Chiba, Japan, under accession number NITE BP-01739 on Oct. 24, 2013. The strain No. 21 is a thermotolerant yeast capable of assimilating xylose to produce ethanol.

The mutant strain according to the present invention is not particularly limited, as long as it is a mutant strain of the strain No. 21 that has xylose assimilation ability and ethanol production ability when cultured at 30° C. under aerobic conditions using a culture medium containing xylose as a sugar source (this mutant strain is sometimes simply referred to as the "present mutant strain" hereinafter). The present mutant strain can be obtained by treating the strain No. 21 with a commonly-known mutation method, such as irradiation with ultraviolet rays or radial rays or contact with a substance acting as a mutagen, and picking a strain that is capable of assimilating xylose to produce ethanol when cultured at 30° C. under aerobic conditions using a culture medium containing xylose as a sugar source.

Examples of the culture medium containing xylose as a sugar source in the present invention include a culture medium containing at least xylose as a sugar component acting as a substrate for ethanol synthesis, and the amount of xylose contained in the culture medium is, for example, 0.5 to 20% and preferably 1.0 to 15%. Examples of such a culture medium containing xylose as a sugar source include a culture medium prepared by adding xylose to any of culture media commonly used for yeasts, such as YPD medium (2% Bacto Peptone, 1% yeast extract, 2% glucose), YPAD medium (2% Bacto Peptone, 1% yeast extract, 2% glucose, 40 µl/ml adenine sulfate), SD medium (2% glucose, 0.67% non-L-amino acid-containing yeast nitrogen base), YM medium (0.3% yeast extract, 0.3% malt extract, 0.5% peptone, 1% glucose), and YP medium (1% yeast extract, 2% peptone). A pure sugar such as glucose, sucrose, or fructose, or a mixture thereof can be added together with xylose, or xylose can be added as the sole sugar source. Adding xylose as the sole sugar source means adding no sugar other than xylose so that only xylose is contained as a sugar component acting as a substrate for ethanol synthesis. Examples of the culture medium containing xylose as the sole sugar source include YPXyl medium (1% yeast extract, 2% peptone, 2% xylose) prepared by adding xylose to YP medium. To the culture medium containing xylose as a sugar source there can be added an auxiliary component, which is an inorganic salt such as ammonium sulfate, magnesium sulfate, or potassium phosphate or is a sugar alcohol.

Furthermore, as the culture medium containing xylose as a sugar source there can be used a culture medium to which a saccharified solution derived from lignocellulosic biomass has been added. The method for preparing the saccharified solution is not particularly limited, and examples of the method include: a preparation method in which a polysaccharide is degraded into assimilable monosaccharides using an enzyme that degrades polysaccharides; and a preparation method in which a polysaccharide is hydrolyzed and degraded into assimilable monosaccharides using microorganisms having the ability to degrade polysaccharides.

In the present invention, culture under aerobic conditions refers to culture in the presence of molecular oxygen. An example of shaking culture is culture at a revolution speed of 60 to 400 rpm (revolution per minute).

For the present mutant strain, having xylose assimilation ability means that the mutant strain is capable of metabolizing xylose. Such xylose assimilation ability can be evaluated by culturing a yeast in a culture medium containing xylose and determining the amount of xylose consumed in the culture medium from the start of the culture as a measure of the ability. Specifically, when xylose is consumed in an amount of 50% or more, preferably 70% or more, more preferably 80% or more during culture of a yeast performed using YPXyl medium under aerobic conditions at 30° C. for 48 hours, the yeast can be considered to have xylose assimilation ability. The amount of xylose consumed can be measured by a commonly-known technique using a high-performance liquid chromatography (HPLC).

For the present mutant strain, having ethanol production ability means that the mutant strain is capable of producing ethanol. Such ethanol production ability can be evaluated by culturing a yeast and determining the amount of ethanol produced in the culture medium from the start of the culture as a measure of the ability. Specifically, when ethanol is produced in an amount of 0.05% w/v or more, preferably 0.1% w/v or more, more preferably 0.2% w/v or more during culture of a yeast performed using YPXyl medium under aerobic conditions at 30° C. for 48 hours, the yeast can be considered to have ethanol production ability. The amount of ethanol produced can be measured by a commonly-known technique using high-performance liquid chromatography (HPLC).

The strain No. 21 and the present mutant strain (which are sometimes collectively referred to as the "present yeast" hereinafter) can be cultured with YPD medium, YPAD medium, SD medium, YM medium, and the like which are commonly used for culture of yeasts.

The present yeast has resistance to various stresses. First of all, the present yeast has resistance to thermal stress and can be grown well even at a high temperature of 47° C. The present yeast has also resistance to oxidative stress and can be successfully grown in a culture medium containing 6 mM of $H_2O_2$. The present yeast further has resistance to osmotic stress and can be successfully grown in a culture medium containing 35% glucose. In addition, the present yeast has resistance to ethanol stress and can be successfully grown in a culture medium containing 10% ethanol.

The present yeast has also glucose resistance. The glucose resistance refers to resistance to the glucose repression mentioned above. That is, the glucose resistance is a measure of the ability to assimilate various sugars to convert them into ethanol. By virtue of having glucose resistance, the present yeast allows efficient ethanol production using a liquid containing various sugars, such as a saccharified solution derived from lignocellulosic biomass.

Furthermore, the present yeast is capable of assimilating xylose to efficiently produce ethanol. When a thermotolerant yeast strain, *Kluyveromyces marxianus* strain DMKU3-1042 (accession number: NITE BP-291, Japanese Patent No. 5051727; sometimes simply referred to as "strain 3-1042" hereinafter), which was isolated by the present inventors in Thailand and which shows high ethanol productivity at 40° C. or more, is used to assimilate xylose, xylitol is obtained as a metabolic product in a larger amount than ethanol, so the efficiency of ethanol production is low. By contrast, when the present yeast is used to assimilate xylose, ethanol is obtained as a metabolic product in a larger amount than xylitol, so the efficiency of ethanol production is high. In particular, when the culture is performed with increased aeration properties, ethanol can account for most of the metabolic products, in addition to which the time taken for ethanol production can be reduced.

The method for producing ethanol according to the present invention is not particularly limited as long as it is a method in which the present yeast is cultured under aerobic conditions using a culture medium containing xylose as a sugar source. Such an ethanol production method according to the present invention allows efficient production of ethanol from xylose.

Given that the present yeast can undergo ethanol fermentation at a high temperature of 30° C. or more, enzymatic saccharification of lignocellulosic biomass and ethanol fermentation can be allowed to take place simultaneously in the culture medium.

The temperature for the culture in the method for producing ethanol according to the present invention is preferably, but not particularly limited to, 30 to 40° C., more preferably 30 to 37° C. Examples of the culture method include shaking culture, stirring culture, shaking-stirring culture, continuous culture, and combinations thereof, and a preferred example is shaking culture or stirring culture. The revolution per minute in the shaking culture is, for example, 60 to 400 rpm, and preferably 80 to 200 rpm. To increase the yeast cell density in a mass culture system, aeration can be performed at a rate of 0.1 to 0.3 vessel volume per minute (vvm). Increasing the aeration properties can make the proportion of produced ethanol higher than that of produced xylitol in the metabolic products resulting from assimilation of xylose. The culture time is, for example, 1 to 10 days, preferably 2 to 7 days, and more preferably 2 to 3 days. The pH of the culture medium is, for example, pH 4 to 8, and preferably pH 5 to 7.

The method for producing ethanol according to the present invention can employ any conventionally known technique for collecting produced ethanol from the culture medium. An example of the technique is one in which a liquid phase containing ethanol and a solid phase containing the yeast and solid components are separated from each other by a solid-liquid separation operation, and then ethanol contained in the liquid phase is collected through separation and purification by distillation.

EXAMPLES (Isolation of Yeast)

In four regions of Laos, samples were taken from fruits, vegetables, leaves of herbaceous plants, and soils. Each sample was implanted on YPD medium and cultured at 37° C. for 3 days. The cultured sample was then spread over a YPD agar plate and cultured at 37° C. for 1 to 2 days, after which the resulting colony was separated. The separated colony was screened to select strains that were thermally tolerant and had high xylose assimilation ability, and one of the strains was designated as No. 21.

(Identification of Yeast)

The strain No. 21 obtained by the above screening was examined for its morphological, physiological, and biochemical characteristics by common methods (Kurtzman and Fell (1998)) etc. As a result, it was found for the strain No. 21 that the colony was cream-colored, moist, glistening, raised with a smooth margin, and viscous and showed multipolar budding, and that ascospores were globose and the number of them was 2 to 4 per ascus. This strain grew and produced ethanol from glucose at 45° C. In addition, genome DNA was extracted from the strain No. 21, and its 26S rDNA base sequence (SEQ ID NO: 1) was determined by the Sanger method and compared with those of known yeast species using BLAST homology search. As a result, the sequence matched 100% to those of known strains of *Kluyveromyces marxianus* (such as strain BM4 and strain NBRC1777). The strain No. 21 was thus identified as *Kluyveromyces marxianus*.

(Resistance to Various Stresses)

To determine the industrial utility of the strain No. 21, its resistance to various stresses which can occur during culture using a yeast was examined. A loopful of the strain No. 21 and a loopful of the strain 3-1042 as a control strain were each inoculated into YPD liquid medium (pH 7.0) and cultured under aerobic conditions at 30° C. for 18 hours to prepare strain stock suspensions. Next, YPD agar medium was prepared, the strain stock suspensions of the strain No. 21 and strain 3-1042 were each diluted with YP liquid medium by factors of 1, 10, 100, 1000, and 10000, and the diluted solutions were respectively spotted on five points of the YPD agar medium in order from the left. Culture was performed under three temperature conditions, i.e., at 30° C., 45° C., and 47° C. for 18 hours to examine the growth. To further examine the resistance to three chemical stresses, oxidative stress (by 5 mM or 6 mM $H_2O_2$), osmotic stress (by 30% or 35% glucose), and ethanol stress (by 8% or 10% ethanol) in addition to the resistance to thermal stress (physical stress) described above, the strain stock suspensions were diluted in the same manner as above, the diluted solutions were spotted on YPD agar media containing the stress sources, and culture was performed to compare the growths.

FIG. 1 shows the results of the various stress resistant tests. The figure is in the form of a matrix, the columns of which show the temperature conditions (30° C., 45° C., and 47° C.), and the rows of which show the various stresses (1. thermal stress, 2. oxidative stress, 3. osmotic stress, and 4. ethanol stress). A row of the strain 3-1042 as a control strain (upper row; shown as DMKU3-1042) and a row of the strain No. 21 (lower row) were spotted on one YPD agar medium plate and were captured together in one photograph.

As for the thermal stress, the strain No. 21 grew well under any of the temperature conditions of 30° C., 45° C., and 47° C. In particular at 47° C., the strain No. 21 grew better than the strain 3-1042 which is a thermotolerant, ethanol-producing strain. This revealed that the strain No. 21 can be used as a thermotolerant strain under high temperature conditions.

As for the oxidative stress, the strain No. 21 showed better growth than the strain 3-1042 under all of the temperature conditions. The strain 3-1042 hardly grew in the presence of 5 mM $H_2O_2$. By contrast, the strain No. 21 grew well at 30° C. and 45° C., and was also discovered to have a certain level of resistance to 5 mM $H_2O_2$ even at 47° C.

As for the osmotic stress, the strain No. 21 showed approximately the same level of resistance as the strain 3-1042. The growth of the strain No. 21 was demonstrated to be good at up to 45° C., albeit slightly poorer than that of the strain 3-1042. The strain No. 21 was thus discovered to be usable under an osmotic stress.

As for the ethanol stress, the strain No. 21 showed better growth than the strain 3-1042 at 30° C. Both of the strains did not grow at all at 45° C. and 47° C. In the presence of 8% ethanol at 30° C., the strain No. 21 showed the same level of growth as under only thermal stress and no chemical stress, which demonstrated that this strain has ethanol resistance.

(Glucose Resistant Test)

The above strain stock suspensions of the strain No. 21 and the strain 3-1042 were each diluted with YP liquid medium by factors of 1, 10, 100, 1000, and 10000, and the diluted solutions were spotted, in order from the left, on the respective five points of YPD agar media each containing any one of various sugars (glucose, galactose, mannose, xylose, and arabinose) as the sole sugar source (each medium contained the corresponding sugar in an amount of 2%). 2-Deoxyglucose (2-DOG) was added in an amount of 0.01%, and culture was performed under three temperature conditions, i.e., at 30° C., 37° C., and 40° C. for 48 hours to examine the glucose resistance. 2-DOG is a substance that is ingested by a glucose transporter but is not metabolized in a glycolytic system, and the addition of 2-DOG can induce glucose repression.

The results are shown in FIG. 2. The figure is in the form of a matrix, the columns of which show the culture temperatures (30° C., 37° C., and 40° C.) and the presence or absence of 2-DOG ([+0.01% 2-DOG] means that 2-DOG was present), and the rows of which show sugar sources (glucose, galactose, mannose, xylose, and arabinose) in the culture media. A row of the strain 3-1042 as a control (upper row) and a row of the strain No. 21 (lower row) were spotted on one YPD agar medium plate and were captured in a photograph, and such photographs are arranged in the figure.

Glucose was a positive control, and both glucose and 2-DOG were ingested by the cells, so that no difference in growth was observed between the two strains.

As for the case of galactose, the growth in the presence of 2-DOG was worse at all of the temperatures of 30° C., 37° C., and 40° C. than in the case of glucose which was a positive control, and glucose repression was observed for both the strain No. 21 and the strain 3-1042. Between the strain No. 21 and the strain 3-1042 there was found no clear difference.

As for the case of mannose, glucose repression was not observed for both the strain No. 21 and the strain 3-1042. This was thought to be due to the property of the yeasts metabolizing mannose independently of the presence of glucose. Also, there was found no clear difference between the strain No. 21 and the strain 3-1042.

As for the case of xylose, glucose repression was observed for both the strain No. 21 and the strain 3-1042. However, the strain No. 21 was less susceptible to the repression effect, which revealed that the strain No. 21 is a strain having glucose resistance. The resistance to 2-DOG was marked particularly at high temperatures (37° C. and 40° C.), which revealed that the strain No. 21 has the ability to assimilate xylose at a high temperature condition of around 40° C. even in a culture fluid in which glucose is present.

As for the case of arabinose, glucose repression was observed for both the strain No. 21 and the strain 3-1042. However, the strain No. 21 was discovered to have higher glucose resistance than the strain 3-1042, particularly at high temperatures (37° C. and 40° C.). The strain No. 21 was demonstrated to be also capable of assimilating arabinose in the presence of glucose.

(Ethanol Production from Xylose-1)

To examine the ability of the strain No. 21 to produce ethanol from xylose, an ethanol production test was conducted using liquid YPXyl medium containing xylose as the sole sugar source. A loopful of the strain No. 21 and a loopful of the strain 3-1042 were each inoculated into 30 mL YPXyl medium (pH 7, containing 2% xylose) and cultured at 30° C. To determine the oxygen requirement for xylose assimilation, the growth and ethanol productivity were examined by performing shaking culture under three conditions, i.e., at 50 rpm, 100 rpm, and 150 rpm. Each culture was performed for 96 hours and, at 24-hour intervals, fractions of the culture fluid were sampled to measure the absorption of $OD_{660}$ (a measure of growth), the xylose concentration in the culture fluid (a measure of xylose assimilation), the xylitol concentration in the culture fluid (a measure of xylose unused for ethanol fermentation), and the ethanol concentration in the culture fluid (a measure of ethanol production ability), respectively. The xylose concentration and the ethanol concentration were determined by centrifuging the culture fluid (at 14,000 rpm for 1 minute), filtering the supernatant with a membrane filter (manufactured by Nihon Pall Ltd.) to prepare a test liquid, and then subjecting the test liquid to measurement by a high-performance liquid chromatograph (manufactured by Hitachi High-Technologies Corporation). As for the conditions of analysis by high-performance liquid chromatography for measuring the ethanol concentration in the culture medium, Gelpack (registered trademark) GL-C610-S (manufactured by Hitachi High-Technologies Corporation) was used as a column.

The results are shown in FIG. 3. The figure is in the form of a matrix, the columns of which show the absorption of $OD_{660}$ (Growth OD660), the xylose concentration in the culture fluid (Xylose % w/v), the xylitol concentration in the culture fluid (Xylitol % w/v), and the ethanol concentration in the culture fluid (Ethanol % w/v), respectively, in order from the left. The rows show the shaking conditions (50, 100, and 150 rpm). In the figure, the results for the strain No. 21 are indicated by pale, gray solid lines (-▲-), while the results for the strain 3-1042 are indicated by dark, gray solid lines (-♦-).

In the case of shaking culture at 50 rpm, both of the strains hardly grew, the xylose concentration in the culture fluid showed almost no change, and ethanol was not produced. This demonstrates that oxygen (aeration) is needed for xylose assimilation.

In the case of shaking culture at 100 rpm, both of the strains proliferated well. Also, the xylose concentration in the culture fluid decreased over time, which demonstrates that each of the strains assimilated xylose. The xylitol concentration in the culture fluid was higher for the strain 3-1042, while the ethanol concentration was higher for the strain No. 21. This result was thought to be because while the strain No. 21 assimilated xylose to undergo ethanol fermentation, the strain 3-1042 used xylose for a metabolic pathway other than ethanol fermentation so that an increased amount of xylitol was formed as a metabolic product. In addition, the strain No. 21 produced 0.3% (w/v) of ethanol in 72 hours.

Also in the case of shaking culture at 150 rpm, both of the strains assimilated xylose and proliferated well as in the case of shaking culture at 100 rpm. For the strain No. 21, the xylitol concentration in the culture fluid was nearly 0%, and the ethanol concentration nearly reached a maximum (0.2% w/v) in 48 hours. It was demonstrated for the strain No. 21 that sufficient aeration promoted the assimilation of xylose, leading to efficient production of ethanol. As for the strain 3-1042, ethanol was scarcely produced (<0.1%) and, instead, xylitol accumulated in the culture fluid.

These results demonstrated that the strain No. 21 is a strain that has the ability to assimilate xylose contained as the sole sugar source in the culture fluid and produce ethanol from xylose. Xylose is a pentose abundantly contained in plant biomass. There has been a problem concerning the assimilation capacity of yeasts thus far, and such a problem has been an obstacle to ethanol production from plant biomass. The strain No. 21, which is the yeast according to the present invention, has been demonstrated to be an excellent yeast strain that resolves the technical problem.

(Ethanol Production from Xylose-2)

The following procedures were employed to verify that the strain No. 21 has the ability to produce ethanol from xylose even at 37° C. A loopful of the strain No. 21, a loopful of the strain 3-1042, and a loopful of *Pichia stipitis* (*P. stipitis*) strain having a high ability to assimilate xylose and produce ethanol were each inoculated into 30 mL YPXyl medium (pH 7, containing 2% xylose), and cultured at 30° C. or 37° C. and at 160 rpm to examine the growth and ethanol productivity. Each culture was performed for 120 hours and, at 12-hour intervals, fractions of the culture fluid were sampled to measure the absorption of $OD_{660}$ (a measure of growth), the xylose concentration in the culture fluid (a measure of xylose assimilation), and the ethanol concentration in the culture fluid (a measure of the ethanol production ability), respectively. The xylose concentration and the ethanol concentration were determined by measurements performed in the same manner as previously described.

The results are shown in FIG. 4. In each graph, the ethanol concentration (% w/v) in the culture fluid is indicated by a pale, gray solid line (-▲-), the xylose concentration (g/L) in the culture fluid is indicated by a dark, gray solid line (-♦-), and the absorption of $OD_{660}$ is indicated by a dark, gray solid line (-■-). In each graph, the upper axis represents the absorption of $OD_{660}$ and the xylose concentration (g/L) in the culture fluid, while the lower axis represents the ethanol concentration (% w/v) in the culture fluid.

It was discovered that the strain No. 21 efficiently produces ethanol using xylose as a sugar source when cultured both at 30° C. and at 37° C., while the strain 3-1042 and the *Pichia stipitis* strain are inferior in efficiency of ethanol production using xylose as a sugar source when cultured at 37° C., although they efficiently produce ethanol using xylose as a sugar source when cultured at 30° C.

INDUSTRIAL APPLICABILITY

The use of the yeast according to the present invention allows efficient production of ethanol by assimilation of xylose, and thus the yeast is useful in the field of ethanol production.

The invention claimed is:

1. A method for producing ethanol, comprising culturing a yeast, *Kluyveromyces marxianus* strain No. 21 (accession number: NITE BP-01739) that has xylose assimilation ability and ethanol production ability when cultured at 30° C. under aerobic conditions using a culture medium containing 0.5-20% xylose as a sugar source.

2. The method for producing ethanol according to claim 1, wherein the culturing is a shaking culture, stirring culture, shaking-stirring culture, continuous culture, or a combination thereof.

3. The method for producing ethanol according to claim 2, wherein the culturing is a stirring culture at a revolution of 60 to 400 rpm.

* * * * *

UNITED STATES PATENT AND TRADEMARK OFFICE
CERTIFICATE OF CORRECTION

PATENT NO. : 10,011,853 B2
APPLICATION NO. : 15/305105
DATED : July 3, 2018
INVENTOR(S) : Mamoru Yamada et al.

Page 1 of 1

It is certified that error appears in the above-identified patent and that said Letters Patent is hereby corrected as shown below:

In the Specification

Column 1, Line 40-42:
Replace "the National Laboratory for Genetic Resources Preservation, 1111 S. Mason Street, Fort Collins, CO, USA" with --NITE Patent Microorganisms Depositary, National Institute of Technology and Evaluation, #122, 2-5-8 Kazusakamatari, Kisarazu-shi, Chiba 292-0818, Japan--

Column 1, Line 47:
Replace "BP-01739 March 16, 2015" with --NITE BP-01739 October 24, 2013--

Column 1, Line 50-51:
Replace "BP-01739 March 16, 2015" with --NITE BP-01739 October 24, 2013--

Signed and Sealed this
Twenty-seventh Day of November, 2018

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 563
<212> TYPE: DNA
<213> ORGANISM: Kluyveromyces marxianus
<220> FEATURE:
<223> OTHER INFORMATION: Inventor: Yamada, Mamoru
```

```
    Inventor: Nitiyon, Sukanya
    Inventor: Keo-oudone, Chansom

<400> SEQUENCE: 1
aatcctcagt cccagctggc tgtattccca cgggctataa cactctaccg aagcagagcc      60
aaaccaaccg ggattgcctt agtaacggcg agtgaagcgg caaaagctca aatttgaaat     120
ctggcgtctt cgacgtccga gttgtaattt gaagaaggcg actttgtagc tggtccttgt     180
ctatgttcct tggaacagga cgtcatagag ggtgagaatc ccgtgtggcg aggatcccag     240
ttatttgtaa agtgctttcg acgagtcgag ttgtttggga atgcagctct aagtgggtgg     300
taaattccat ctaaagctaa atattggcga gagaccgata gcgaacaagt acagtgatgg     360
aaagatgaaa agaactttga aaagagagtg aaaaagtacg tgaaattgtt gaaagggaag     420
ggcatttgat cagacatggc gtttgcttcg gctttcgctg ggccagcatc agttttagcg     480
gttggataaa tcctcgggaa tgtggctctg cttcggtaga gtgttatagc ccgtgggaat     540
acagccagct gggactgagg att                                             563
```